United States Patent [19]

Park et al.

[11] 4,085,132

[45] Apr. 18, 1978

[54] PROCESS FOR THE PRODUCTION OF HYDROXYALKYLPHENYL DERIVATIVES

[75] Inventors: Kyong P. Park, Cranston; Anthony F. Vellturo, North Kingstown, both of R.I.

[73] Assignee: Ciba-Geigy Corporation, Ardsley, N.Y.

[21] Appl. No.: 589,984

[22] Filed: Jun. 24, 1975

Related U.S. Application Data

[63] Continuation of Ser. No. 505,303, Sep. 12, 1975, abandoned, which is a continuation of Ser. No. 318,810, Dec. 27, 1972, abandoned.

[51] Int. Cl.$^2$ ............................ C07C 69/54; C07C 69/76
[52] U.S. Cl. ................................. 560/75; 260/45.85 B
[58] Field of Search .................................... 260/473 S

[56] References Cited

U.S. PATENT DOCUMENTS

| Re. 27,004 | 12/1970 | Meier et al. | 260/473 |
| 2,916,532 | 12/1959 | Schmerling et al. | 260/473 |
| 2,927,085 | 3/1960 | Gordon et al. | 260/473 |
| 2,927,086 | 3/1960 | Gordon et al. | 260/473 |
| 3,642,868 | 2/1972 | Dexter et al. | 260/473 |

FOREIGN PATENT DOCUMENTS

| 1,337,163 | 7/1963 | France | 260/473 |
| 54,376 | 3/1967 | Germany | 260/473 |
| 1,001,098 | 8/1965 | United Kingdom | 260/473 |

*Primary Examiner*—Paul J. Killos
*Attorney, Agent, or Firm*—Nestor W. Shust

[57] ABSTRACT

An improved process for the production of hydroxyalkylphenyl derivatives, especially esters containing hydroxyalkylphenyl groups is disclosed, which process comprises gradually adding methyl acrylate, in the presence of an alkaline catalyst, to the alkyl substituted phenolic compound and a suitable alcohol. The improved process results in good yields and in a reduction of undesirable by-products while avoiding isolation of the intermediates.

4 Claims, No Drawings

PROCESS FOR THE PRODUCTION OF HYDROXYALKYLPHENYL DERIVATIVES

This is a continuation of application Ser. No. 505,303 filed on Sept. 12, 1975 which is a cont. of application Ser. No. 318,810 filed on Dec. 27, 1972 both now abandoned.

DETAILED DISCLOSURE

Conventional methods for the production of different kinds of hydroxyalkylphenyl derivatives, particularly esters thereof, involve multi-step reaction procedures, such as transesterification of carboxylic acid-lower-alkyl esters containing hydroxyalkylphenyl groups. Said esters in their turn, are first prepared, e.g., by reacting corresponding alkylphenols with methyl acrylate, followed either by isolating the resultant intermediate ester and subsequent transesterification thereof, or direct transesterification of the reaction product from the reaction melt. Isolation of the intermediate ester, though enabling production of the desired end product in good yields and reduction of by-products, requires the use of very substantial amounts of suitable solvents. The disposal of said solvents creates serious effluent problems under present day anti-pollution requirements. Direct transesterification of the reaction melt, on the other hand, results in the formation of considerable quantities of by-products from polymers and diesters present in the melt, and hence in poor yields of the desired end-products.

The present invention provides an improved, simplified process by which various kinds of esters containing hydroxyalkylphenyl groups can be produced in good yields, without isolation of the intermediates, while undesirable by-products are kept at a minimum.

More specifically, the invention provides an improved process for the production of compounds having the formulae

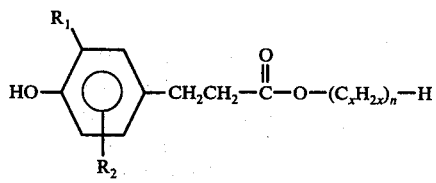   I,

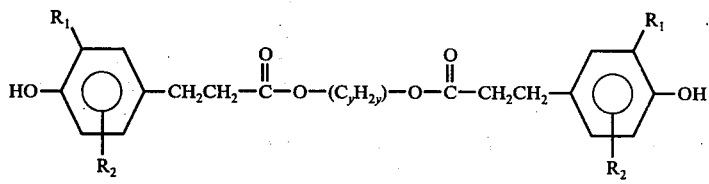   II,

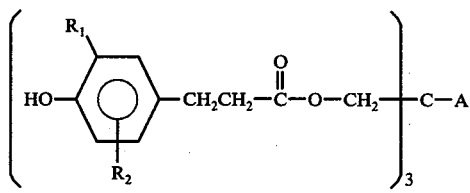   III or

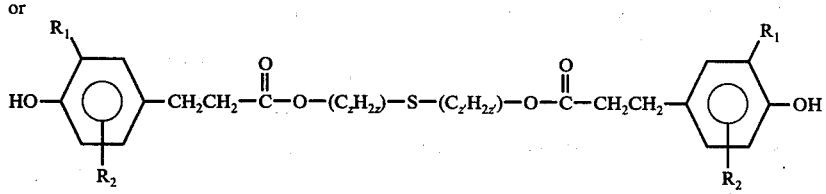   IV in which formulae
$R_1$ and $R_2$ independently of each other represent an alkyl group having from 1 to 6 carbon atoms,
$x$ has a value from 6 to 30, inclusively,
$y$ has a value from 2 to 8, inclusively,
each of $z$ and $z'$ have a value from 2 to 12, inclusively, and
A represents —$CH_2CH_3$ or a radical of the formula

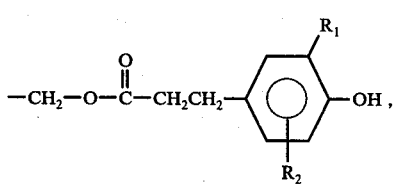

wherein $R_1$ and $R_2$ are as defined above.

This process comprises gradually adding methyl acrylate to a phenol of the formula

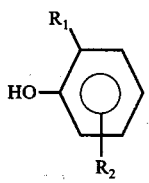   V and an alcohol selected from
(a) a monohydric alcohol of the formula

   Ia, (b) a dihydric alcohol of the formula
HO—(C$_y$H$_{2y}$)—OH  IIa, (c) a tri- or tetrahydric alcohol of the formula

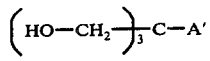  IIIa (d) a thioether of the formula
HO—(C$_z$H$_{2z}$)—S—(C$_{z'}$H$_{2z'}$)—OH  IVa wherein
R$_1$, R$_2$, x, y, z and z' are as defined above,
and
A' represents —CH$_2$CH$_3$ or —CH$_2$OH, in the presence of from 0.001 to 10 mole percent, based on the phenol compound of formula V, of an alkaline catalyst.

Alkyl groups represented by R$_1$ or R$_2$ can be straight or branched. Representative of such alkyl groups are thus methyl, ethyl, n-propyl, isopropyl, n-, sec- or tert-butyl, n-pentyl, sec-pentyl, neopentyl and n-hexyl. Preferably one, and most preferably both, of R$_1$ and R$_2$ are branched alkyl groups, such as isopropyl, and, more especially, tert-butyl. The alkyl radical designated by R$_2$ is either in a position para to R$_1$ or, preferably, in the other ortho position to the hydroxyl group.

For illustration purposes some specific examples of compounds of formulae I to IV are mentioned.

Compounds of Formula I n-hexyl-β-(2-methyl-5-t-butyl-hydroxyphenyl) propionate n-octyl-β-(3,5-di-t-butyl-4-hydroxyphenyl) propionate n-decyl-β-(3-ethyl-5-t-butyl-4-hydroxyphenyl) propionate n-dodecyl-β-(3-ethyl-5-t-butyl-4-hydroxyphenyl) propionate n-hexadecyl-β-(3-n-hexyl-5-isopropyl-5-hydroxyphenol)propionate n-octadecyl-β-(3,5-di-t-butyl-4-hydroxyphenyl) propionate.

Compounds of Formula II ethylene-bis-β-(3,5-di-t-butyl-4-hydroxyphenyl)propionate isopropylene-bis-β-(3-methyl-5-t-butyl-4-hydroxyphenyl)propionate n-butylene-bis-62 -(3,5-di-isopropyl-4-hydroxyphenyl)propionate n-hexylene-bis-β-(3,5-di-t-butyl-4-hydroxyphenyl)-propionate n-heptylene-bis-β-(3,5-di-t-butyl-4-hydroxyphenyl)-propionate n-octylene-bis-β-(3,5-di-t-butyl-4-hydroxyphenyl)-propionate.

Compounds of Formula III 1,1,1-trimethylol-propane-{3-(3',5'-di-t-butyl-4'-hydroxyphenyl)-propionate} pentaerythritol tetrakis-{3-(2'-methyl-5'-t-butyl-4'-hydroxyphenyl)-propionate} pentaerythritol tetrakis-{3-(3',5'-di-t-butyl-4'-hydroxyphenyl)-propionate}.

Compounds of Formula IV thio-bis-{ethylene-3-(3,5-di-t-butyl-4-hydroxyphenyl)propionate} thio-bis-{isopropylene-3-(3,5-di-t-butyl-4-hydroxyphenyl)propionate}.

Examples of suitable phenol compounds of Formula V to be used in the improved process according to the invention are:

2-methyl-6-isopropyl-phenol
2-t-butyl-5-methylphenol
2-methyl-6-t-butyl-4-phenol
2-isopropyl-5-ethylphenol
2-ethyl-6-butylphenol
2,6-di-isopropyl-phenol
2-n-hexyl-6-isopropyl-phenol
2,5-di-t-butyl-phenol.

As illustrative examples of monohydric, dihydric, tri- and tetrahydric alcohols and thioether compounds of Formulae Ia to IVa the following may be mentioned:

Monohydric Alcohols
n-hexyl
n-octyl
n-decyl
n-dodecyl
n-hexadecyl
n-octadecyl

Dihydric Alcohols
1,2-ethyleneglycol
1,2-propanediol
1,3-propanediol
1,4-butanediol
2,5-hexanediol
1,6-hexanediol
1,7-heptanediol
1,8-octanediol Tri- and Tetrahydric Alcohols
1,1,1-trimethylolpropane
pentaerythritol Thioether Compounds
bis-(β-hydroxyethyl)-sulfide(thiodiglycol)
bis-(β-hydroxypropyl)sulfide.

Preferred compounds of Formulae I to IV, and Ia to IVa, respectively, are those wherein R$_1$ and R$_2$ are ortho to the hydroxyl group, each of R$_1$ and R$_2$ being a branched alkyl group, more particularly t-butyl, x has a value from 12 to 24, inclusively,
y has a value from 2 to 6 inclusively,
each of z and z' have a value of 2 or 3, and
A' represents —CH$_2$OH.

The most preferred compounds of Formulae I to IV are n-octadecyl-β-(3,5-di-t-butyl-4-hydroxyphenyl)propionate, ethylene-bis-β-(3,5-di-t-butyl-4-hydroxyphenyl)propionate, hexylene-1,6-bis-β-(3,5-di-t-butyl4-hydroxyphenyl)propionate, pentaerythritol tetrakis{3-(3',5'-di-t-butyl-4'-hydroxyphenyl)propionate} and thiobis-{ethylene-3-(3,5-di-t-butyl-4-hydroxyphenyl)propionate}.

Suitable alkaline catalysts to be used in the process of the instant invention are alkali metal hydrides, alkali metal alkoxides of the formula

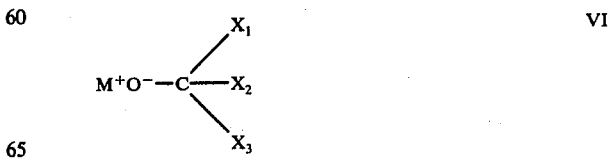  VI wherein
M is an alkali metal ion, and $X_1$, $X_2$ and $X_3$ independently of each other represent hydrogen, alkyl, aryl or arylalkyl groups having up to about 12 carbon atoms, and alkali metal amides of the formula

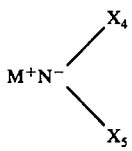    VII wherein

M is as defined above, and $X_4$ and $X_5$ independently of each other represent hydrogen, alkyl or aryl groups having up to about 12 carbon atoms.

Alkyl radicals represented by $X_1$, $X_2$, $X_3$, $X_4$, and $X_5$ are preferably methyl or ethyl groups, while aryl and arylalkyl radicals designated by one or more of said symbols are, e.g., phenyl, benzyl, or phenethyl groups. Suitable alkali metals are lithium, potassium and sodium.

Examples of suitable alkaline catalysts are thus lithium, sodium and potassium hydrides, sodium and potassium methoxides, ethoxides, propoxides, isopropoxides, t-butoxides, sodium 1,1-dimethylbutoxides, potassium benzyloxide, sodium benzyl-isopropoxide, lithium, potassium and sodium amides, lithium N-methylamide and N-ethylamide, lithium N,N-dimethylamide and sodium N-methyl-N-phenylamide.

Among the alkali metal amides of Formula VII those are preferred wherein M is the sodium or potassium ion and $X_4$ and $X_5$ each represent hydrogen.

It is, however, particularly preferred to employ alkali metal alkoxides of Formula VI as the alkaline catalysts more especially those wherein M is the sodium or potassium ion, and $X_1$, $X_2$ and $X_3$ each represent hydrogen or methyl, or $X_1$ represents hydrogen, $X_2$ represents hydrogen or methyl and $X_3$ represents methyl.

Although the alkaline catalysts may be employed in amounts ranging from 0.001 to 10 mole percent, based on the phenol compound of Formula V, amounts of from about 1 to 5 mole percent are preferred.

The gradual addition of methyl acrylate to a phenol of Formula V and an alcohol of Formulae Ia to IVa in the presence of an alkaline catalyst represents a critical feature of the present process. Care should be taken that methyl acrylate is fed to the reaction mixture at a constant slow rate throughout the reaction so as to keep the methyl acrylate concentration in the reaction mixture to a minimum and thereby minimize the formation of undesirable by-products, such as polymers and diesters. Throughout the gradual addition of methyl acrylate and until completion of the reaction, the reaction mixture is conveniently heated to a temperature between about 80° and 140° C, more particularly 100° and 120° C, under nitrogen. The overall molar ratio of methyl acrylate and the phenol compound of Formula V should be at least 1:1, preferably, a slight excess, e.g., an excess of about 5 to 30 mole percent, of methyl acrylate is used. Small amounts of an aliphatic alcohol, such as methyl alcohol, ethyl alcohol or isopropyl alcohol, or a dipolar aprotic solvent, such as dimethylsulfoxide or dimethyl formamide, may be added to the reaction mixture so as to improve the conversion.

After the completion of the reaction, the resultant ester of Formulae I to IV is isolated and purified by conventional methods, e.g., by acidifying the reaction mass, e.g., with glacial acetic acid and crystallizing the product from a suitable organic solvent such as aliphatic hydrocarbons, e.g., hexane or heptane, and lower aliphatic alcohols, e.g., methyl alcohol, ethyl alcohol and isopropyl alcohol.

The compounds of Formulae I to IV are obtained in high yields and substantially free from undesirable by-products. These compounds are known per se and can be used for the stabilization of organic materials normally subject to oxidative deterioration according to known procedures.

Materials which can be stabilized with the compounds of Formulae I to IV include synthetic organic polymeric substances such as vinyl resins formed from the polymerization of vinyl halides or from the copolymerization of vinyl halides with unsaturated polymerizable compounds, e.g., vinyl esters, $\alpha,\beta$-unsaturated acids, $\alpha,\beta$-unsaturated esters, $\alpha,\beta$-unsaturated ketones, $\alpha,\beta$-unsaturated aldehydes and unsaturated hydrocarbons such as butadienes and styrene; poly-$\alpha$-olefins such as polyethylene, polypropylene, polybutylene, polyisoprene and the like, including copolymers of poly-$\alpha$-olefins; polyurethanes prepared from polyols such as propylene glycol or ethylene glycol and organic polyisocyanates; polyamides such as polyhexamethylene adipamide; polyesters such as polymethylene terephthalates; polycarbonates; polyacetals; polystyrene, polyethylene oxide; and copolymers such as those of high impact polystyrene containing copolymers of butadiene and styrene and those formed by the copolymerization of acrylonitrile, butadiene and/or styrene. Other materials which can be stabilized with the compounds of Formulae I to IV include lubricating oils of the aliphatic ester type, e.g., di-(2-ethylhexyl)-azelate, pentaerythritol tetracaproate and the like; animal and vegetable derived oils, e.g., linseed oil, fat, tallow, lard, peanut oil, cod liver oil, castor oil, palm oil, corn oil, cotton seed oil and the like; hydrocarbon materials such as gasoline, both natural and synthetic, diesel oil, mineral oil, fuel oil, drying oil, cutting fluids, waxes, resins and the like, fatty acids such as soaps and the like.

In general, the stabilizer compounds of Formulae I to IV are employed in amounts of from about 0.005% to about 10% by weight of the material to be stabilized. A particularly advantageous range for polyolefins such as polypropylene is from about 0.1% to about 1%.

The following examples serve to illustrate the process of this invention.

EXAMPLE 1

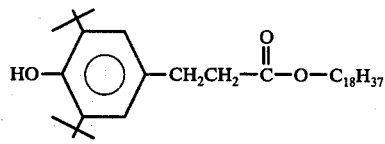

To a 500 ml. 3-necked flask, equipped with a stirrer, a condenser, a thermometer, a calibrated dropping funnel and a nitrogen inlet were charged 85.8 g of 2,6-di-t-butylphenol and 105 g of n-octadecyl alcohol. The flask content was heated to 90° C. Vacuum was applied to dry the melt. Then the vacuum was released with nitrogen. 1.0 g of sodium methoxide was added, and the melt was heated to 105 to 108° C. Over a two hour period and at a constant rate 37.3 g of methyl acrylate were added from the dropping funnel. After the methyl acrylate addition was complete, the reaction mixture was held for four hours at 105° C to 108° C. Vacuum was applied and the pressure was carefully reduced to approximately 15 mm Hg. The reaction mixture was then slowly heated in 2 hours to 130° C and was held at this temperature and under reduced pressure for three hours. The flask content was cooled to 60° C and 1.8 g of glacial acetic acid were added, followed by 165 g of 90% aqueous isopropyl alcohol. The resultant solution was clarified into a 500 ml flask and 292 g of 90% aqueous isopropyl alcohol were added to the filtrate. At approximately 37° C, the solution was seeded with 0.5 g of n-octadecyl$\beta$-(3,5-di-t-butyl-4-hydroxyphenyl)propionate.

The product crystallized and the slurry was cooled to approximately 15° C. The product was isolated on a Buchner funnel, washed with cold isopropyl alcohol, sucked dry and dried in a vacuum oven at approximately 36° C to a constant weight. 166 g of dry n-octadecyl-$\beta$-(3,5-di-t-butyl4-hydroxyphenyl)propionate were obtained; m.p. 52.5° C; yield 80% based on the n-octadecyl alcohol used.

EXAMPLE 2

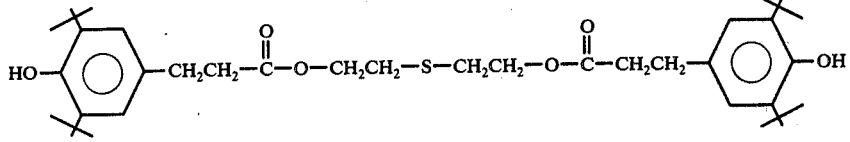

To a 500 ml. 3 necked flask, equipped with a stirrer, a condenser, a thermometer, a calibrated dropping funnel and a nitrogen inlet were charged 85.8 g of 2,6-di-t-butylphenol and 22 g of thiodiglycol. The flask content was heated to 90° C. Vacuum was applied to dry the melt. Then the vacuum was released with nitrogen. 2.8 g of potassium t-butoxide were added, and the melt was heated to 105 to 108° C. Over a two hour period and at a constant rate 37.3 g of methyl acrylate were added from the dropping funnel. After the methyl acrylate addition was completed, the reaction mixture was held for 4 hours at 105° C to 108° C. Vacuum was applied and the pressure was carefully reduced to approximately 15 mm Hg. The reaction mixture was then slowly heated in 2 hours to 130° C and was held at this temperature and under reduced pressure for 3 hours. The flask content was cooled to 60° C and 2.5 g of glacial acetic acid were added, followed by 95 g of ethyl alcohol. The resultant solution was filtered into a 500 ml flask, the filtrate thus obtained was cooled to 20° C and seeded with 0.5 g of thio-bis-{ethylene-3-(3,5di-t-butyl-4-hydroxyphenyl)propionate}.

The reaction product crystallized and the resulting slurry was cooled to 16° C. The product was isolated on a Buchner funnel, washed with cold ethyl alcohol, sucked dry and dried in a vacuum oven at 50° C to a constant weight. 58.0 g of dry thio-bis{ethylene-3-(3,5-di-t-butyl-4-hydroxyphenyl)propionate} were obtained; m.p. 71.5° C.

EXAMPLE 3

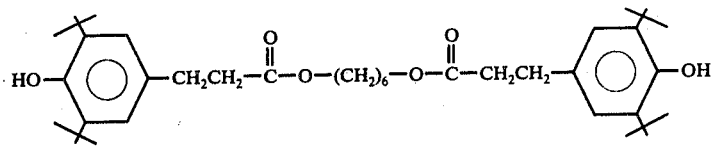

Following the procedure described in Example 2 except for using 23.6 g of 1,6-hexanediol in place of thiodiglycol, hexylene-1,6-bis-$\beta$-(3,5-di-t-butyl-4-hydroxyphenyl)propionate is obtained in good yields.

What is claimed is:

1. In the process for the production of a compound having the formula

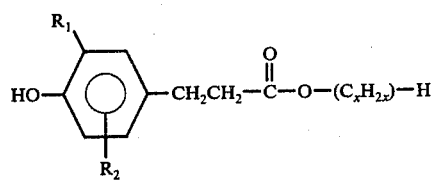

wherein
$R_1$ and $R_2$ independently of each other represent an alkyl group having from 1 to 6 carbon atoms and
x has a value from 6 to 30, inclusively, which comprises reacting methyl acrylate with a phenol of the formula

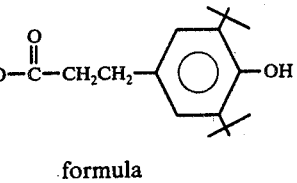

and thereafter with a monohydric alcohol of the formula $$HO-(C_xH_{2x})-H \qquad Ia,$$

in the presence of an alkaline catalyst, the improvement which consists essentially of
a. gradually adding methyl acrylate to the reaction mixture which comprises said phenol, monohydric alcohol and a catalyst, without isolating the intermediate.

2. A process of claim 1 wherein $R_2$ is in the ortho position to the hydroxyl group and each $R_1$ and $R_2$ are branched alkyl.

3. A process of claim 2 wherein $R_1$ and $R_2$ are tert-butyl and x has a value of 12 to 24.

4. A process as claimed in claim 1, for the production of n-octadecyl-$\beta$-(3,5-di-t-butyl-4-hydroxyphenyl)propionate, which comprises gradually adding methyl acrylate to 2,6-di-t-butylphenol and n-octadecyl alcohol.

* * * * *